US008896293B2

(12) United States Patent  
Kordonski et al.

(10) Patent No.: US 8,896,293 B2
(45) Date of Patent: *Nov. 25, 2014

(54) METHOD AND APPARATUS FOR MEASUREMENT AND CONTROL OF MAGNETIC PARTICLE CONCENTRATION IN A MAGNETORHEOLOGICAL FLUID

(75) Inventors: William Kordonski, Webster, NY (US); Keith Beadle, Webster, NY (US); Sergei Gorodkin, Rochester, NY (US); Arpad Sekeres, Rochester, NY (US)

(73) Assignee: QED Technologies International, Inc., Aurora, IL (US)

( * ) Notice: Subject to any disclaimer, the term of this patent is extended or adjusted under 35 U.S.C. 154(b) by 318 days.

This patent is subject to a terminal disclaimer.

(21) Appl. No.: 13/085,688

(22) Filed: Apr. 13, 2011

(65) Prior Publication Data

US 2012/0164916 A1 Jun. 28, 2012

Related U.S. Application Data

(63) Continuation-in-part of application No. 12/977,180, filed on Dec. 23, 2010.

(51) Int. Cl.
- *G01N 27/74* (2006.01)
- *G01R 33/12* (2006.01)
- *B24B 57/02* (2006.01)
- *B24B 49/10* (2006.01)

(52) U.S. Cl.
CPC ............. *B24B 57/02* (2013.01); *B24B 49/10* (2013.01); *G01N 27/74* (2013.01)
USPC ......................................... 324/204

(58) Field of Classification Search
CPC .................. B24B 49/10; B24B 49/105
USPC ......... 324/201, 224, 258, 239, 222, 223, 228, 324/234, 236, 240, 337, 92, 93, 94, 204
See application file for complete search history.

(56) References Cited

U.S. PATENT DOCUMENTS

| | | | | |
|---|---|---|---|---|
| 5,795,212 | A * | 8/1998 | Jacobs et al. | 451/36 |
| 6,577,118 | B2 * | 6/2003 | Parent et al. | 324/204 |
| 2003/0020463 | A1 * | 1/2003 | Carlson et al. | 324/204 |
| 2004/0189290 | A1 * | 9/2004 | Lehman et al. | 324/230 |
| 2008/0214092 | A1 * | 9/2008 | Kordonski et al. | 451/36 |

* cited by examiner

*Primary Examiner* — Reena Aurora
(74) *Attorney, Agent, or Firm* — Thomas E Omholt; Robert C Brown; Arlene Hornilla

(57) ABSTRACT

A system for sensing and controlling concentration of magnetic particles in magnetorheological fluid comprising a wire coil and an AC voltage generator that, when energized, creates a magnetic flux field including a fringing field. When the fringing field extends through the magnetorheological fluid, the impedance in the circuit is proportional to the concentration of magnetic particles. A reference wire coil identical to the sensing wire coil is connected therewith. A demodulator is connected to each of the coils sends an impedance difference signal to a feedback controller connected to controllable dispensing apparatus for adding a calculated amount of replenishing fluid to the magnetorheological fluid. The system may be incorporated into an integrated fluid management module having apparatus for receiving and replenishing spent magnetorheological fluid and a sensor system in accordance with the present invention for use in a magnetorheological finishing system having a carrier wheel.

3 Claims, 5 Drawing Sheets

METHOD AND APPARATUS FOR MEASUREMENT AND CONTROL OF MAGNETIC PARTICLE CONCENTRATION IN A MAGNETORHEOLOGICAL FLUID

RELATIONSHIP TO OTHER APPLICATIONS AND PATENTS

The present application is a Continuation-In-Part of a pending application Ser. No. 12/977,180, filed Dec. 23, 2010.

BACKGROUND OF THE INVENTION

1. Field of the Invention

The present invention relates to systems for magnetically-assisted abrasive finishing and polishing of substrates; more particularly, to such systems employing magnetorheological (MR) polishing fluids; and most particularly, to a method and apparatus for measurement and control of the concentration of magnetic particles in a magnetorheological fluid.

2. Background of the Invention

Use of magnetically-stiffened magnetorheological fluids for abrasive finishing and polishing of substrates is well known. Such fluids, containing magnetically-soft abrasive particles dispersed in a liquid carrier, exhibit magnetically-induced thixotropic behavior in the presence of a magnetic field. The apparent viscosity of the fluid can be magnetically increased by many orders of magnitude, such that the consistency of the fluid changes from being nearly watery to being a very stiff paste. When such a paste is directed appropriately against a substrate surface to be shaped or polished, for example, an optical element, a very high level of finishing quality, accuracy, and control can be achieved.

In an exemplary MR polishing interface, a convex lens (also referred to herein as a "workpiece") to be polished is installed at some fixed distance from a moving wall, so that the lens surface and the wall form a converging gap. Typically, the lens is mounted for rotation about an axis thereof. An electromagnet, placed below the moving wall, generates a non-uniform magnetic field in the vicinity of the gap. The magnetic field gradient is normal to the wall. The MR polishing fluid is delivered to the moving wall just above the electromagnet pole pieces to form a polishing ribbon. As the ribbon moves in the field, it acquires plastic Bingham properties and the top layer of the ribbon is saturated with abrasive due to levitation of non-magnetic abrasive particles in response to the magnetic field gradient. Thereafter, the ribbon, which is pressed against the wall by the magnetic field gradient, is dragged through the gap resulting in material removal from the lens in the lens contact zone. This area is designated as the "polishing spot" or "work zone". The rate of material removal in the polishing spot can be controlled by controlling the strength of the magnetic field, the geometrical parameters of the interface, and the wall velocity.

The polishing process employs a computer program to determine a CNC machine schedule for varying the velocity (dwell time) and the position of the rotating workpiece through the polishing spot. Because of its conformability and subaperture nature, this polishing tool may finish complex surface shapes like aspheres having constantly changing local curvature.

A fundamental advantage of MRF over competing technologies is that the polishing tool does not wear, since the recirculating fluid is continuously monitored and maintained. Polishing debris and heat are continuously removed. The technique requires no dedicated tooling or special setup. Integral components of the MRF process are the MRF software, the CNC platform with programmable logic control, the MR fluid delivery and recirculating/conditioning system, and the magnetic unit with incorporated carrier surface. The carrier surface can be formed, for example, by the rim of a rotating wheel, by horizontal surface of a rotating disk, or by a continuous moving belt.

In a typical prior art magnetorheological finishing system, a carrier surface is formed on a vertically-oriented non-magnetic wheel having an axially-wide rim which is undercut symmetrically about a hub. Specially-shaped magnetic pole pieces, which are symmetrical about a vertical plane containing the axis of rotation of the wheel, are extended toward opposite sides of the wheel under the undercut rim to provide a magnetic work zone on the surface of the wheel, preferably at about the top-dead-center position. The carrier surface of the wheel may be flat, i.e., a cylindrical section, or it may be convex, i.e., a spherical equatorial section, or it may be concave. The convex shape can be particularly useful as it permits finishing of concave surfaces having a radius longer than the radius of the wheel.

Mounted above the work zone is a workpiece receiver, such as a chuck, for extending a workpiece to be finished into the work zone. The chuck is programmably manipulable in a plurality of modes of motion and is preferably controlled by a programmable controller or a computer.

Magnetorheological polishing fluid, having a predetermined concentration of non-magnetic abrasive particles and magnetic particles which are magnetically soft, is extruded in a non-magnetized state, typically from a shaping nozzle, as a ribbon onto the work surface of the wheel, which carries it into the work zone where it becomes magnetized to a pasty consistency. In the work zone, the pasty MR polishing fluid does abrasive work on the substrate. The exposure of the MR fluid to air causes some evaporation of carrier fluid and a consequent concentrating of the MR fluid. Exiting the work zone, the concentrated fluid becomes non-magnetized again and is scraped from the wheel work surface for replenishment and reuse.

Fluid delivery to, and recovery from, the wheel is managed by a closed fluid delivery system. Operation of the prior art MR finishing system requires use of a delivery system which comprises a delivery pump, a suction pump, a flow meter, a viscometer, a nozzle, pressure transducers, a pulse dampener, a magnetic valve, a chiller, and tubing. Cost of such a delivery system is significant and may constitute up to quarter of the total cost of the MR finishing system.

Recharging of the delivery system is a time-consuming process, requiring complete disassembling, cleaning of all components, re-assembly, and breaking in after charging with a fresh fluid, which lengthy procedure negatively affects productivity and flexibility of technology.

The delivery system must operate in a non-stop regime during the MR fluid's "life" in the machine. Continuous recirculation of abrasive MR fluid is required even in the intervening periods between polishing in order to avoid changes in MR fluid properties due to sedimentation of solids. Such continuous recirculation results in accelerated wear and tear of delivery system components and consumption of extra energy.

MR fluid flow rate instability (pulsations) in the delivery system due to any of several causes results in unstable removal rate and errors on the substrate surface.

To provide proper circulation of MR fluid and compatibility with different components of the delivery system, the fluid must have specific rheological/viscous properties and appropriate chemistry. This limits selection of fluid components and restricts fluid composition, for example, for greater solids concentration required for enhancement of the removal rate.

What is needed in the art is an improved, low cost, low maintenance and technologically flexible MR finishing system wherein the polishing operation does not require a prior art conventional MR fluid delivery system, and wherein an appropriate apparatus and method for direct measurement and dynamic control of the concentration of magnetic particles in the MR fluid is employed.

It is a principal object of the present invention to continuously monitor and control the concentration of magnetic particles in an MR fluid in an MR finishing system.

SUMMARY OF THE INVENTION

Briefly described, an improved system for magnetorheological finishing of a substrate in accordance with the present invention incorporates an improved sensor system that is sensitive to concentration of magnetic particles in the fluid and exerts dynamic control of MR fluid properties to control water content in the MR fluid. The sensor system includes a reference coil and a sensing coil joined in an electrical circuit. The sensing coil is positioned adjacent to a chamber containing the MR fluid to be monitored such that a fringing field of the sensing coil extends into the MR fluid. When the face of the sensor is brought in contact with an MR fluid, the reactance of the coil is changed resulting in a corresponding change of impedance. Coil impedance is measured and an output signal is produced using an appropriate electronic means.

The system may also contain means to compensate for thermal variations in circuit impedance. For example, the sensor may comprise two identical coils which are in thermal contact: a sense coil and a reference coil. They are driven by a high-frequency sine-wave excitation, and their differential impedance is measured using a sensitive demodulator. Differencing the two coils' outputs provides a sensitive way to measure the MR fluid permeability (which is proportional to concentration of magnetic particles), while cancelling out variations caused by temperature. A signal from the sensor provides input to a feedback controller that causes a water dispensing subsystem to add a calculated amount of water to the MR fluid to restore the fluid to a desired particle concentration.

BRIEF DESCRIPTION OF THE DRAWINGS

The foregoing and other objects, features, and advantages of the invention, as well as presently preferred embodiments thereof, will become more apparent from a reading of the following description in connection with the accompanying drawings in which.

DETAILED DESCRIPTION OF THE INVENTION

The principle of measurement of the magnetic permeability of a material (MR Fluid) and of an apparatus in accordance with the present invention is as follows.

Figure 2:
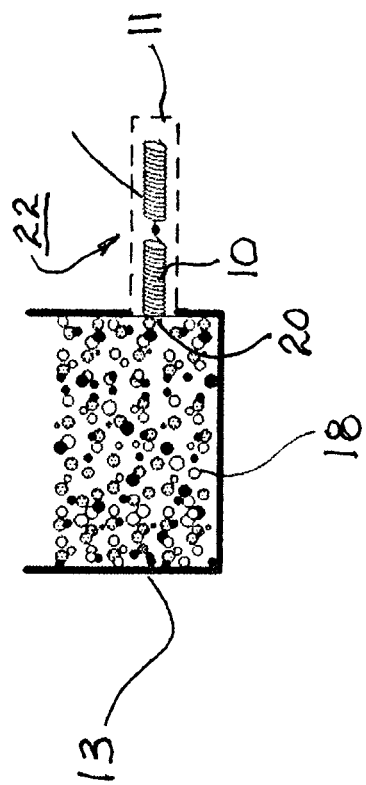
FIG. 2 is a schematic view of a temperature-compensated sensor disposed in close proximity to a sample of MR fluid in accordance with the present invention.
Figure 1:
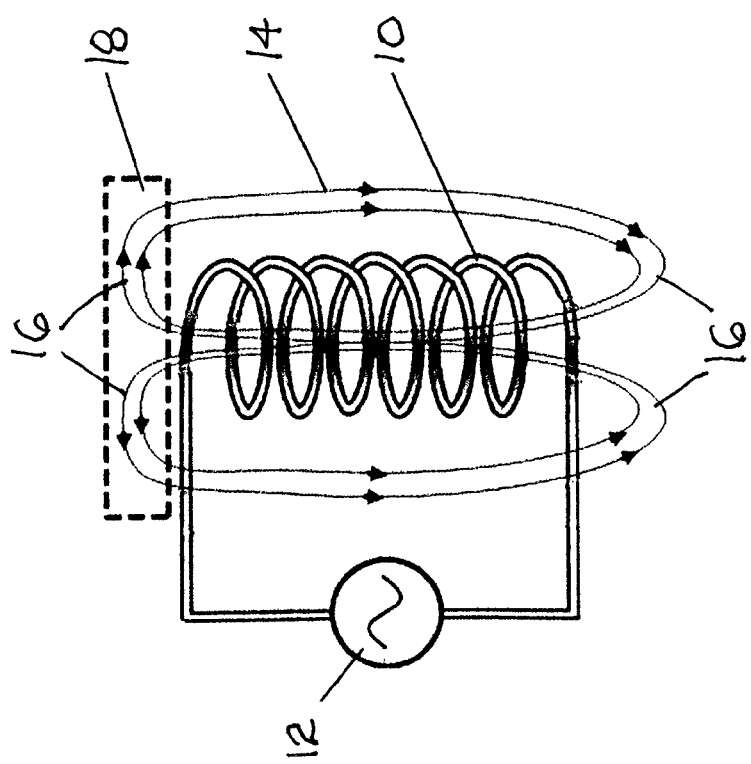
FIG. 1 is a schematic view of a magnetic coil having a fringing field extending into a sample of MR fluid.

Referring to FIGS. 1 and 2, a wire coil 10 is connected to an AC voltage generator 12, resulting in a magnetic field 14 in known fashion. Magnetic field 14 includes regions of so-called fringing fields 16 beyond each end of coil 10. A sample of a magnetic material 18 such as MR fluid in which magnetic permeability is to be measured is placed next to coil 10 within fringing field 16. When a voltage is applied to coil 10, a magnetic circuit is formed to conduct a magnetic flux generated by the coil. The circuit consists of two main components: coil 10 and sample 18. Applying Ampere's circuital law to the circuit and assuming that the leakage flux is negligible we see that:

$$NI = H_c l_c + H_s l_s \quad (1)$$

where NI is coil magnetomotance (N is number of turns and I is the current); the subscript c refers to the coil and s to the sample; $H_c$ and $H_s$ are magnetic field intensities and $l_c$ and $l_s$ are the path lengths in corresponding elements.

The flux of magnetic induction is the same over any cross-section of the magnetic circuit:

$$\Phi = B_c A_c = B_s A_s \quad (2)$$

Where $\Phi$=flux intensity, and $B_c$ and $B_s$ are magnetic inductions, and $A_c$ and $A_s$ the cross-sections of coil 10 and sample 18, respectively.

Taking into account that:

$$H_c = \frac{B_c}{\mu_0} \text{ and } H_S = \frac{B_s}{\mu} \quad (3)$$

where $\mu_0$ is permeability of vacuum and $\mu$ is permeability of sample 18, and combining these three equations, we obtain $$NI = B_c A_c \left[ \frac{l_c}{\mu_0 A_c} + \frac{l_s}{\mu A_s} \right] \quad (4)$$

Thus, the magnetic flux will be:

$$\Phi = B_c A_c = \frac{NI}{\frac{l_c}{\mu_0 A_c} + \frac{l_s}{\mu A_s}} \quad (5)$$

where $$\frac{l_c}{\mu_0 A_c} = R_c \text{ and } \frac{l_s}{\mu A_s} = R_s$$

are reluctances of coil 10 and sample 18, respectively.

The magnetic flux $\Phi$ is therefore equal to the magnetomotance divided by the sum of the reluctances of the coil and of the sample. At all circuit parameters constant, some change of the reluctance of sample 18 results in a corresponding change of the magnetic flux in the coil and thereby its inductance:

$$L_c = \frac{N\Phi}{I} = \frac{N^2}{R_c + R_s} \quad (6)$$

Therefore, measurements of coil inductance allow determination of sample reluctance and eventually of sample permeability.

The magnetic permeability μ depends on magnetic properties of MR fluid. In turn, these properties are dependent on concentration of the magnetic particles φ in the sample, as given by Equation 7:

$$\mu = f(\phi) \quad (7)$$

When all parameters of the system, including the AC voltage applied to coil 10, are held constant, any variation in concentration of magnetic particles in the MR Fluid contacting the face 20 of a sensor 22 containing coil 10 will result in a corresponding change of the coil's inductance.

A convenient way to determine the coil inductance is by measurement of coil's inductive reactance which is a measure of the opposition to current flow in alternating current circuit:

$$X_L = \omega L \quad (8)$$

Here ω is the frequency of alternating current.

Figure 3:
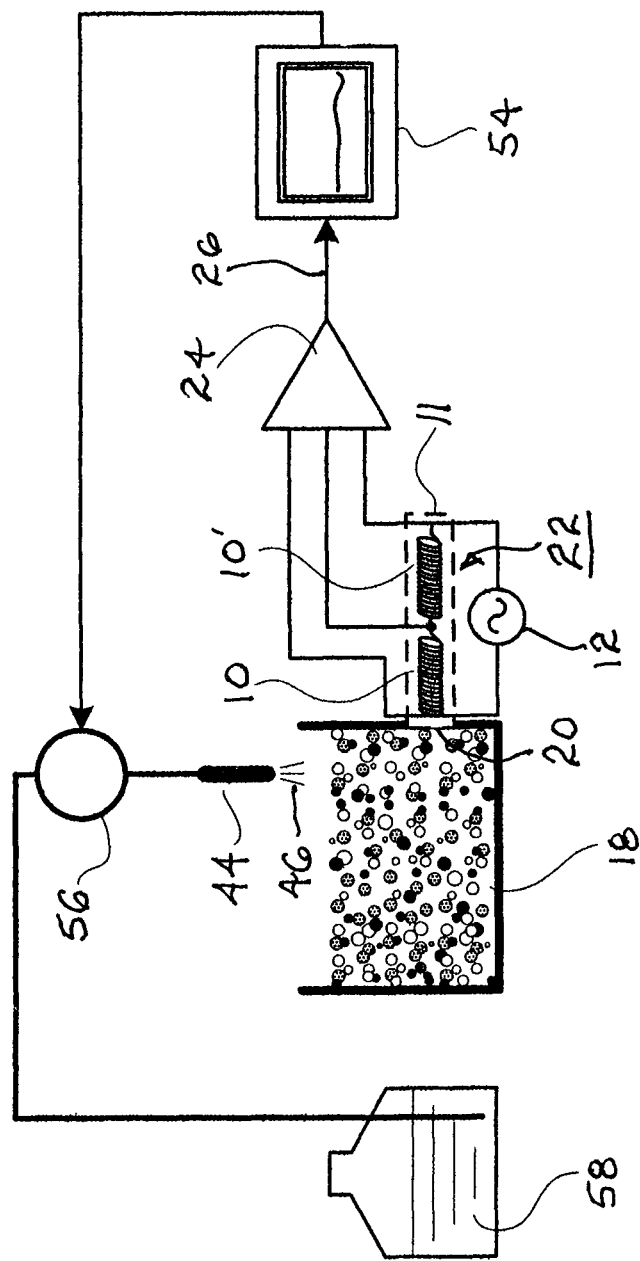
FIG. 3 is a schematic view of a system for measuring and dynamically controlling the magnetic particle concentration of an MR fluid in accordance with the present invention.

Referring to FIG. 3, in practice, MR fluid concentration is measured as follows. Coil 10 within a non-conductive housing 11 forms a sensing element. When the face 20 of sensor 22 is brought in contact with an MR fluid such that fringing field 16 extends into the fluid, the reactance of sensing coil 10 is changed, resulting in a corresponding change of impedance. Coil impedance is measured and an output signal is produced using an appropriate electronic means. The system further may contain means to compensate for thermal variations in circuit impedance. For example, as shown in FIG. 3, sensor 22 comprises two identical coils 10,10' which are in thermal contact: a sense coil 10 and a reference coil 10'. They are driven by a high-frequency sine-wave excitation, and their differential impedance is measured using a sensitive demodulator 24. Differencing the outputs of coils 10,10' provides a sensitive way to measure permeability of MR fluid 18, while cancelling out variations caused by temperature. Another way (not shown) to compensate for temperature is through measurement of coil temperature and producing an appropriate feed-back signal for compensation. For example, such a signal can be generated by measuring the coil's resistance in DC circuit or using an appropriate thermo-sensor like a thermocouple or thermistor embedded in the coil.

In doing so, the system output signal follows variations in the sample magnetic particles concentration. In the general case, it can be defined as shown in Eq. (9):

$$V_s = f(\phi, k_1, k_2 \ldots) \quad (9)$$

where $k_1, k_2 \ldots$ are some constant parameters which depend on system geometry and system electrical parameters. The magnitude of the sensor output signal can be manipulated by (pre) setting the different system parameters such as number of turns and geometries of the coils, frequency and voltage of the oscillator, impedance of components, and the like.

A quantitative relationship between the concentration of magnetic particles in MR fluid 18 and the output voltage $V_s$ 26 of demodulator 24 is determined by calibration with samples having known magnetic particle concentrations. Such calibration gives the general expression according to Equation 10:

$$\phi = aV_s + b \quad (10)$$

where a and b are constants defined by calibration.

Example

Figure 4:
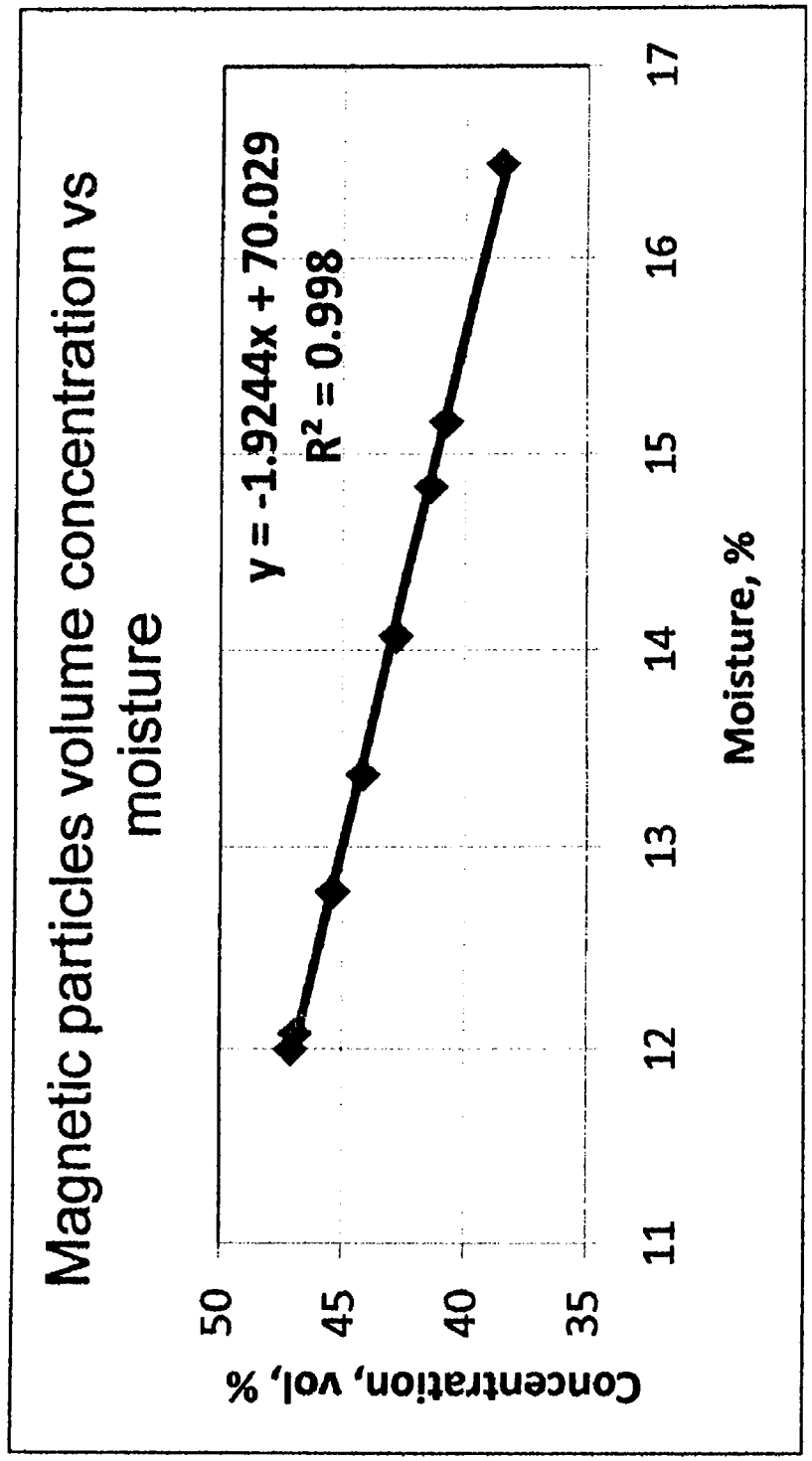
FIG. 4 is a graph showing dependence of the volume percent concentration as a function of moisture percent.
Figure 5:
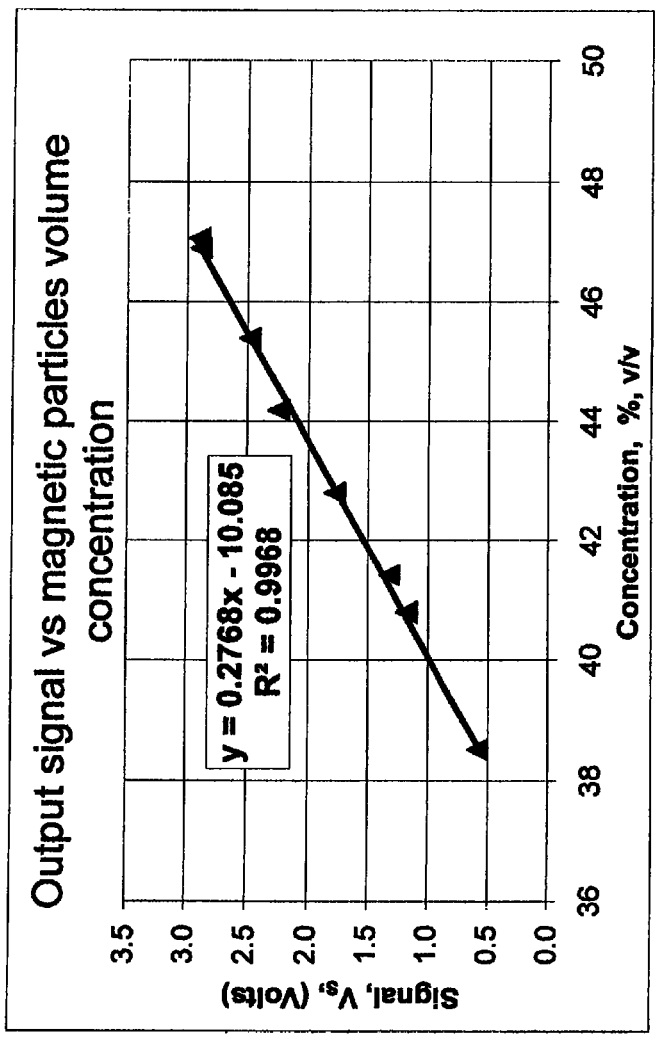
FIG. 5 is a graph showing output signal in volts from the system shown in FIG. 3 as a function of the volume percent concentration of magnetic particles in the MR fluid.

Samples of water-based MR fluid were used for testing and system calibration. Initially, the concentration of magnetic particles in MR fluid was determined by measurements of moisture (percent of water), which defines the concentration of magnetic particles, with Moisture Analyzer HB43, available from Mettler-Toledo Gmbh, Switzerland. Corresponding data are shown in FIG. 4. Then, the MR fluid with known concentration of magnetic particles was placed in container 13 having flush mounted sensor 22, and signal 26 proportional to concentration of magnetic particles was generated by sensor 22 comprising two coils 10,10' embedded in a water-proof case 11 as shown in FIG. 3. FIG. 5 shows an excellent linear dependence of voltage on concentration in the range of measured concentrations as predicted by Equation 10.

Figure 6:
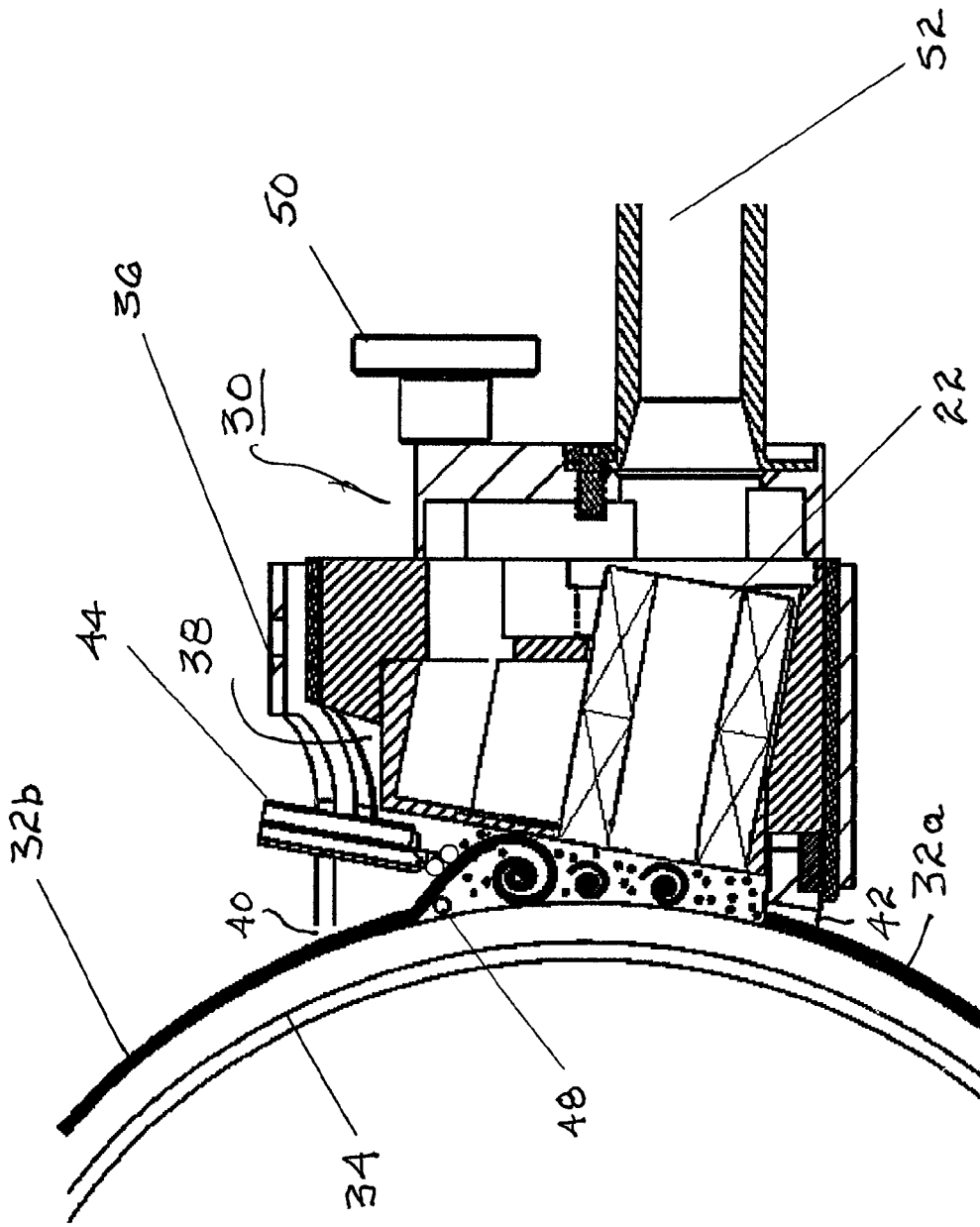
FIG. 6 is an elevational cross-sectional view of an embodiment of the present invention incorporated in an Integrated Fluid Flow Management module (IFMM) as disclosed in the parent US patent application, the relevant portions of which are herein incorporated by reference.

Referring to FIGS. 3 and 6, and disclosed in the parent application, in a magnetorheological finishing machine, IFMM 30 is arranged to remove spent ribbon 32b from wheel 34, replenish and retemper the spent MR fluid, and extrude a ribbon 32a of replenished MR fluid onto the wheel.

IFMM 30 comprises a generally cylindrical, cup-shaped housing 36 formed of a shielding material to prevent magnetization of MR fluid within the IFMM. Housing 36 is provided with a surface around the open end of housing 36 that is preferably conformable to the surface of wheel 34. Housing 36 contains a chamber 38 having an entrance slot 40 for admitting ribbon 32b and an exit slot 42 for dispensing extruded ribbon 32a. A dripper tube 44 provides access to chamber 38 for dispensing of fluids 46 (FIG. 3) thereinto, e.g., MR fluid, replenishment fluid, and the like. A ribbon deflector line 48 extends across the inner end of entrance slot 40 and rides in contact with the surface of wheel 34 to deflect spent ribbon 32b from wheel 34 into chamber 38. Line 48 is tensioned by knob 50 and may be made of nylon, stainless steel, copper, and the like. An electric mixer motor and mixer impeller are disposed on housing and extend into chamber 38 for mixing fluids 46 with spent MR fluid 32b to produce replenished MR fluid 32a for reuse. Sensor 22 is disposed in a wall of chamber 38 in contact with mixed and replenished MR fluid 34a for determining the concentration of magnetic particles therein. Electrical conduit 52 permits passage of electrical leads to the mixer motor and sensor.

In operation, the magnetically-shielded (from external field) IFMM cavity 38 is charged with a given volume of MR fluid (for example, by a syringe through the opening in the shield) while wheel 34 rotates. The surface of wheel 34 carries out the low-viscosity MR polishing fluid 32a through exit slot 42, thus forming a ribbon on the wheel surface.

After passing through a work zone (not shown) on wheel 34, the ribbon, now 32b, enters magnetically-shielded IFMM cavity 38, demagnetizes, and is removed from the wheel surface by deflector line 48, forming a jet which along with the moving wheel surface agitates MR fluid and facilitates mixing with replenishment carrier fluid 46, e.g., water injected by dripper 44. Additional agitation/mixing (for example, in the case of the use of relatively viscous MR fluids) can be provided with suitable means such as an optional rotating mixer impeller driven by motor incorporated in the module body.

In accordance with the present invention, the process of ribbon formation and MR polishing fluid recovery in the IFMM cavity is continuous. Typically, water-based MR polishing fluid is used in optics finishing. Overall system stability and removal rate stability are essential for controlled, high-resolution, deterministic finishing. Material removal rate may change due to water evaporation that occurs on the ribbon surface and in the IFMM cavity. This, in turn, causes undesirable change (increase) in MR fluid solids concentration which is detected by sensor 22 incorporated in the cavity wall. (Note: the sensor face or cavity wall separating sensor 22 from chamber 38 preferably is formed from, or coated with, a highly resistant non-ferromagnetic material such as ceramic or diamond to prevent erosion of the sensor face or wall by hard, abrasive magnetic particles during use.) Signal 26 from sensor 22 feeds a conventional feed-back loop controller 54 to activate a water injector pump 56 to inject some specific amount of water 46, drawn from a reservoir 58, to replenish the MR fluid by diluting spent fluid 32b to replenished fluid 32a.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

What is claimed is:

1. An integrated fluid management module for use in a magnetorheological finishing system having a carrier wheel, comprising:
   a) a housing having a magnetically-shielded chamber therein, said chamber having an opening to a surface of said carrier wheel;
   b) apparatus for receiving and replenishing spent magnetorheological fluid within said chamber; and
   c) a ribbon extruder mounted to said housing for extruding a ribbon of replenished magnetorheological fluid from said chamber onto said wheel surface,
   wherein said replenishing apparatus comprises,
   i. a sensor system for determining concentration of magnetic particles in said spent magnetorheological fluid, wherein said sensor system comprises a first wire coil disposed in a housing defining a sensor having only one end in liquid contact with said magnetorheological fluid and an AC voltage generator attached to said first wire coil in an electrical circuit, such that when said generator is energized a magnetic flux field is created in and around said first wire coil, wherein said magnetic flux field includes fringing fields extending beyond the opposite ends of said first wire coil, and wherein, when either but not both of said fringing fields extending beyond the opposite ends of said first wire coil also extends through said magnetorheological fluid, the impedance in said circuit is proportional to said concentration of magnetic particles, and a second wire coil connected to said generator and identical to said first wire coil and having fringing fields outside of said magnetorheological fluid, wherein said first wire coil is a sensing coil and said second wire coil is a reference coil; and
   ii. a controllable dispensing apparatus for adding a calculated amount of replenishing fluid to said spent magnetorheological fluid,
   wherein impetus for receiving and replenishing said spent magnetorheological fluid within said chamber and for extruding said ribbon of replenished magnetorheological fluid from said chamber onto said wheel surface is provided by the motion of said carrier wheel past said integrated fluid management module.

2. A module in accordance with claim 1 wherein said sensor further comprises a demodulator connected to said sensing coil and said reference coil; and a feedback controller connected to said demodulator for sending signals to said controllable dispensing apparatus.

3. A module in accordance with claim 1 wherein said controllable dispensing apparatus comprises:
   a) a source of replenishment fluid;
   b) a pump connected to said source; and
   c) an apparatus connected to said pump for adding said calculated amount of replenishment fluid into said magnetorheological fluid.

* * * * *